United States Patent

Kovesdi et al.

[11] Patent Number: 5,210,026
[45] Date of Patent: May 11, 1993

[54] HUMAN MK GENE AND METHOD OF EXPRESSION

[75] Inventors: Imre Kovesdi, Pearl River; Peter Bohlen, Peekskill, both of N.Y.

[73] Assignee: American Cyanamid Company, Wayne, N.J.

[21] Appl. No.: 650,795

[22] Filed: Feb. 5, 1991

Related U.S. Application Data

[63] Continuation-in-part of Ser. No. 568,573, Aug. 20, 1990, abandoned.

[51] Int. Cl.$^5$ .................. C12P 21/02; C12N 15/12; C12N 1/21; C12N 15/70
[52] U.S. Cl. .................... 435/69.1; 435/320.1; 435/252.3; 435/252.33; 435/172.3; 536/23.5
[58] Field of Search ............... 435/69.1, 172.3, 320.1, 435/69.4, 252.3, 252.33; 935/66, 73; 536/27

[56] References Cited

PUBLICATIONS

Matsubara et al. J. Biol. Chem. vol. 265:9441, 1990.
Kadomatsu et al. Biochem Biophy. Res. Com. 151:1312 1988.
Tomomura et al. J. Biol. Chem. 265:10765. 1990.
Suggs et al. PNAS. 78:6613. 1981.

Primary Examiner—Richard A. Schwartz
Assistant Examiner—John LeGuyader
Attorney, Agent, or Firm—Karen A. Lowney

[57] ABSTRACT

The invention relates to novel DNA and amino sequences for a human MK protein. Also described are expression vectors and host cells useful in a method for production of the MK protein.

14 Claims, 11 Drawing Sheets

```
  1 CGGGCGAAGCAGCGCGGGCAGCGAG

26 ATG CAG CAC CGA GGC TTC CTC CTC CTC ACC CTC CTC GCC CTG CTG GCG CTC ACC
-22  M   Q   H   R   G   F   L   L   L   T   L   L   A   L   L   A   L   T

80 TCC GCG GTC GCC AAA AAG AAA GAT AAG GTG AAG AAG GGC GGC CCG GGG AGC GAG
 -4  S   A   V   A   K   K   K   D   K   V   K   K   G   G   P   G   S   E

134 TGC GCT GAG TGG GCC TGG GGG CCC TGC ACC CCC AGC AGC AAG GAT TGC GGC GTG
 15  C   A   E   W   A   W   G   P   C   T   P   S   S   K   D   C   G   V

188 GGT TTC CGC GAG GGC ACC TGC GGG GCC CAG ACC CAG CGC ATC CGG TGC AGG GTG
 33  G   F   R   E   G   T   C   G   A   Q   T   Q   R   I   R   C   R   V

242 CCC TGC AAC TGG AAG AAG GAG TTT GGA GCC GAC TGC AAG TAC AAG TTT GAG AAC
 51  P   C   N   W   K   K   E   F   G   A   D   C   K   Y   K   F   E   N

296 TGG GGT GCG TGT GAT GGG GGC ACA GGC ACC AAA GTC CGC CAA GGC ACC CTG AAG
 69  W   G   A   C   D   G   G   T   G   T   K   V   R   Q   G   T   L   K

350 AAG GCG CGC TAC AAT GCT CAG TGC CAG GAG ACC ATC CGC GTC ACC AAG CCC TGC
 87  K   A   R   Y   N   A   Q   C   Q   E   T   I   R   V   T   K   P   C

404 ACC CCC AAG ACC AAA GCA AAG GCC AAA GCC AAG AAA GGG AAG GGA AAG GAC TAG
105  T   P   K   T   K   A   K   A   K   A   K   K   G   K   G   K   D   *

458 ACGCCAAGCCTGGATGCCAAGGAGCCCCTGGTGTCACATGGGGCCTGGCCACGCCCTCCCTCTCCCAGGC
528 CCGAGATGTGACCCACCAGTGCCTTCTGTCTGCTCGTTAGCTTTAATCAATCATGCCCTGCCTTGTCCCT
598 CTCACTCCCCAGCCCCACCCCTAAGTGCCCAAAGTGGGGAGGGACAAGGGATTCTGGGAAGCTTGAGCCT
668 CCCCCAAAGCAATGTGAGTCCCAGAGCCCGCTTTTGTTCTTCCCCACAATTCCATTACTAAGAAACACAT
738 CAAATAAACTGACTTTTTCCCCCCAATAAAGCTCTTCTTTTTAATATAAAAAAAAAAAA
```

FIG. 1

```
1   CGGGCGAAGCAGCGGGCAGCGAG

26  ATG CAG CAC CGA GGC TTC CTC ACC CTC GCG CTC ACC
-22  M   Q   H   R   G   F   L   T   L   A   L   T

80  TCC GCG GTC GCC AAA AAG AAA GAT AAG GGC CTG CTG GCG CTC ACC
-4   S   A   V   A   K   K   K   D   K   G   L   L   A   L   T
         ↑

134 TGC GCT GAG TGG GCC TGC ACC CCC AGC AAG GAT TGC CCG GGG AGC GAG
15   C   A   E   W   A   C   T   P   S   K   D   C   P   G   S   E

188 GGT TTC CGC GAG GGC ACC TGC CCC CAG GCC CAG ACC CGC ATC CGG TGC AGG GTG
33   G   F   R   E   G   T   C   P   Q   A   Q   T   R   I   R   C   R   V

242 CCC TGC AAC TGG AAG AAG GAG TTT GGA GCC GAC TGC AAG TAC AAG TTT GAG AAC
51   P   C   N   W   K   K   E   F   G   A   D   C   K   Y   K   F   E   N

296 TGG GGT GCG TGT GAT GGG GGC ACA GGC ACC AAA GTC CGC CAA GGC ACC CTG AAG
69   W   G   A   C   D   G   G   T   G   T   K   V   R   Q   G   T   L   K

350 AAG GCG CGC TAC AAT GCT CAG TGC CAG GAG ACC ATC CGC GTC ACC AAG CCC TGC
87   K   A   R   Y   N   A   Q   C   Q   E   T   I   R   V   T   K   P   C

404 ACC CCC AAG ACC AAA GCA AAG GCC AAA GCC AAG AAA GGG AAG GGA AAG GAC TAG
105  T   P   K   T   K   A   K   A   K   A   K   K   G   K   G   K   D   *

458 ACGCCCAAGCCTGGATGCCAAGGAGCCCTGGTGTCACATGGGCCTGGCCTGGCCACGCCCCTCCTCCCAGGC
528 CCGAGATGTGACCCACCAGTGCCTTCTGTCTGCTCGTTAGCTTTAATCAATCATGCCCTGCCTTGTCCCT
598 CTCACTCCCCAGCCCACCCCAGCCCCAAAGTGGGAGGACAAGGGATTCTGGGAAGCTTGAGCCT
668 CCCCAAAGCAATGTGAGTCCCAGAGCCCGCTTTGTTCTTCCCCACACATTCCATTACTAAGAAACACAT
738 CAAATAAACTGACTTTTCCCCCCAATAAAAGCTCTTTTTTTAATATAAAAAAAAAA
```

```
        1   G   K   K   E   K   P   E   K   K   V   K   K   S   D   C   G   E
HBNF    1  GGG AAG AAA GAG AAA CCA GAA AAA AAA GTG AAG AAG TCT GAC TGT GGA GAA
           XXX XXX XX  XX      X   XX      X       X   XX  XX  X   XX
MK      1  AAA AAG AAA GAT AAG GTG AAG AAG GGC GGC CCG GGG AGC GAG TGC GCT GAG
        1   K   K   K   D   K   V   K   K   G   G   P   G   S   E   C   A   E

18   V   Q   W   S   V   C   V   P   T   S   G   D   C   G   L   G   T
HBNF   52  TGG CAG TGG AGT GTG TGT GTG CCC ACC AGT GGA GAC TGT GGG CTG GGC ACA
           XXX     XXX X       XX      XXX X X XX      XX  XX  XX  XX  XX
MK     52  TGG GCC TGG GGG CCC TGC ACC CCC AGC AGC AAG GAT TGC GGC GTG GGT TTC
       18   V   A   W   G   P   C   T   P   S   S   K   D   C   G   V   G   F

35   R   E   G   T   R   T   G   A   E   C   K   Q   T   M   K   T   Q
HBNF  103  CGG GAG GGC ACT CGG ACT GGA GCT GAG TGC AAG CAA ACC ATG AAG ACC CAG
           XX  XXX XXX XX                      XXX X       X   XX  X
MK    103  CGC GAG GGC ACC  -   -   -   -   -  TGC GGG GCC CAG ACC CAG CGC ATC
       35   R   E   G   T   -   -   -   -   -   C   G   A   Q   T   Q   R   I

52   R   C   K   I   P   C   N   W   K   K   Q   F   G   A   E   C   K
HBNF  154  AGA TGT AAG ATC CCC TGC AAC TGG AAG AAG CAA TTT GGC GCG GAG TGC AAA
           X   XX  X X  X   XXX XXX XXX XXX XXX XX  X   XXX XX  XX  X   XXX XX
MK    139  CGG TGC AGG GTG CCC TGC AAC TGG AAG AAG GAG TTT GGA GCC GAC TGC AAG
       47   R   C   R   V   P   C   N   W   K   K   E   F   G   A   D   C   K
```

FIG. 2

```
         69  Y   Q   F   Q   A   W   G   E   C   D   L   N   T   A   L   K   T
HBNF 205    TAC CAG TTC CAG GCC TGG GGA GAA TGT GAC CTG AAC ACA GCC CTG AAG ACC
            xxx xx xx   xx   x xxx xx   x  xxx xx   x   x xxx xx       xx    x
MK   190    TAC AAG TTT GAG AAC TGG GGT GCG TGT GAT GGG GGC ACA GGC ACC AAA GTC
         64  Y   K   F   E   N   W   G   A   C   D   G   G   T   G   T   K   V 86  R   T   G   S   L   K   R   A   L   H   N   A   E   C   Q   K   T
HBNF 256    AGA ACT GGA AGT CTG AAG CGA GCC CTG CAC AAT GCC GAA TGC CAG AAG ACT
              x   xx  x xxx xxx      xx  x  xx xxx xx   x xxx xxx xx xx
MK   241    CGC CAA GGC ACC CTG AAG AAG GCG CGC TAC AAT GCT CAG TGC CAG GAG ACC
         81  R   Q   G   T   L   K   K   A   R   Y   N   A   Q   C   Q   E   T 103  V   T   I   S   K   P   C   G   K   L   T   K   P   K   P   Q   A
HBNF 307    GTC ACC ATC TCC AAG CCC TGT GGC AAA CTG ACC AAG CCC AAA CCT CAA GCA
             xx  x  xx  xx xxx xxx xx        x xxx xx   x  xx   x   xx xx
MK   292    ATC CGC GTC ACC AAG CCC TGC ACC CCC AAG ACC AAA GCA AAG GCC AAA GCC
         98  I   R   V   T   K   P   C   T   P   K   T   K   A   K   A   K   A 120  E   S   K   K   K   K   E   G   K   K   Q   E   K   M   L   D
HBNF 358    GAA TCT AAG AAG AAG AAA AAG GAA GGC AAG AAA CAG GAG AAG ATG CTG GAT
              x       x  xxx      xx   x   x
MK   343    AAG AAA GGG AAG GGA AAG GAC TAG
        115  K   K   G   K   G   K   D   x 137  x
HBNF 409    TAA
```

FIG. 2 (cont.)

```
          1  K   K   K   E   K   V   K   K   G   -   -   -   S   E   C   S   E
MOU    1  AAA AAA AAA GAG AAG GTG AAG AAG GGC  -   -   -  AGC GAG TGT TCG GAG
              x   x                                        x   x   x
HUM    1  AAA AAG AAA GAT AAG GTG AAG AAG GGC GGC CCG GGG AGC GAG TGC GCT GAG
          1  K   K   K   D   K   V   K   K   G   G   P   G   S   E   C   A   E

15  V   P   V   G   P   C   T   P   S   S   K   D   C   G   M   G   F
MOU   43  TGG ACC TGG GGG CCC TGC ACC CCC AGC AGC AAG GAC TGC GGC ATG GGC TTC
              x                                       x       x   x
HUM   52  TGG GCC TGG GGG CCC TGC ACC CCC AGC AGC AAG GAT TGC GGC GTG GGT TTC
         18  V   A   V   G   P   C   T   P   S   S   K   D   C   G   V   G   F

32  R   E   G   T   C   G   A   Q   T   Q   R   V   H   C   K   V   P
MOU   94  CGC GAG GGT ACC TGT GGG GCC CAG ACC CAG CGC GTC CAT TGC AAG GTG CCC
              x   x                                   x   xx  x
HUM  103  CGC GAG GGC ACC TGC GGG GCC CAG ACC CAG CGC ATC CGG TGC AGG GTG CCC
         35  R   E   G   T   C   G   A   Q   T   Q   R   I   R   C   R   V   P

49  C   N   V   K   K   E   F   G   A   D   C   K   Y   K   F   E   S
MOU  145  TGC AAC TGG AAG AAG GAA TTT GGA GCC GAC TGC AAA TAC AAG TTT GAG AGC
                                       x                           x       x
HUM  154  TGC AAC TGG AAG AAG GAG TTT GGA GCC GAC TGC AAG TAC AAG TTT GAG AAC
         52  C   N   V   K   K   E   F   G   A   D   C   K   Y   K   F   E   N
             ─────────────────────────────────────►

66  V   G   A   C   D   G   S   T   G   T   K   A   R   Q   G   T   L
MOU  196  TGG GGG GCG TGT GAT GGG AGC ACT GGC ACC AAA GCC CGC CAA GGG ACC CTG
              x                   x   x           x           x
HUM  205  TGG GGT GCG TGT GAT GGG GGC ACA GGC ACC AAA GTC CGC CAA GGC ACC CTG
         69  V   G   A   C   D   G   G   T   G   T   K   V   R   Q   G   T   L

83  K   K   A   R   Y   T   A   Q   C   Q   E   T   I   R   V   T   K
MOU  247  AAG AAG GCG CGG TAC ACT GCC CAG TGC CAG GAG ACC ATC CGC GTG ACT AAG
                          x   x   x                                   x   x
HUM  256  AAG AAG GCG CGC TAC AAT GCT CAG TGC CAG GAG ACC ATC CGC GTC ACC AAG
         86  K   K   A   R   Y   N   A   Q   C   Q   E   T   I   R   V   T   K
                         ◄─────────────────────────────────────

100  P   C   T   S   K   T   K   S   K   T   K   A   K   K   G   K   G
MOU  298  CCC TGC ACC TCC AAG ACC AAG TCA AAG ACC AAA GCC AAG AAA GGA AAA GGA
                          x           xx  x                       x   x
HUM  307  CCC TGC ACC CCC AAG ACC AAA GCA AAG GCC AAA GCC AAG AAA GGG AAG GGA
        103  P   C   T   P   K   T   K   A   K   A   K   A   K   K   G   K   G

117  K   D   *
MOU  349  AAG GAC TAG

HUM  358  AAG GAC TAG         FIG. 3
        120  K   D   *
```

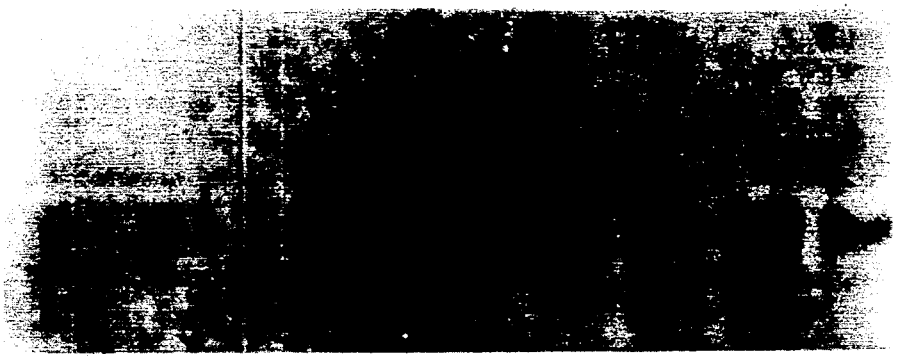
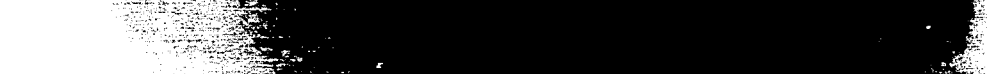
FIG. 6

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 799 Base Pairs 143 Amino Acids (B) TYPE: Nucleic Acid and Amino Acid
(C) STRANDEDNESS: Single
(D) TOPOLOGY: Linear (ii) MOLECULE TYPE: DNA and Protein (xi) SEQUENCE DESCRIPTION: SEQ ID NO: 1:

```
CGGGCGAAGC AGCGCGGGCA GCGAG                                              25

ATG CAG CAC CGA GGC TTC CTC CTC CTC ACC CTC CTC                          61
Met Gln His Arg Gly Phe Leu Leu Leu Thr Leu Leu
 1               5                  10

GCC CTG CTG GCG CTC ACC TCC GCG GTC GCC AAA AAG                          97
Ala Leu Leu Ala Leu Thr Ser Ala Val Ala Lys Lys
         15                  20

AAA GAT AAG GTG AAG AAG GGC GGC CCG GGG AGC GAG                         133
Lys Asp Lys Val Lys Lys Gly Gly Pro Gly Ser Glu
 25              30                  35

TGC CGT GAG TGG GCC TGG GGG CCC TGC ACC CCC AGC                         169
Cys Arg Glu Trp Ala Trp Gly Pro Cys Thr Pro Ser
             40                  45

AGC AAG GAT TGC GGC GTG GGT TTC CGC GAG GGC ACC                         205
Ser Lys Asp Cys Gly Val Gly Phe Arg Glu Gly Thr
     50                  55                  60

TGC GGG GCC CAG ACC CAG CGC ATC CGG TGC AGG GTG                         241
Cys Gly Ala Gln Thr Gln Arg Ile Arg Cys Arg Val
                 65                  70

CCC TGC AAC TGG AAG AAG GAG TTT GGA GCC GAC TGC                         277
Pro Cys Asn Trp Lys Lys Glu Phe Gly Ala Asp Cys
         75                  80

AAG TAC AAG TTT GAG AAC TGG GGT GCG TGT GAT GGG                         313
Lys Tyr Lys Phe Glu Asn Trp Gly Ala Cys Asp Gly
 85                  90                  95

GGC ACA GGC ACC AAA GTC CGC CAA GGC ACC CTG AAG                         349
Gly Thr Gly Thr Lys Val Arg Gln Gly Thr Leu Lys
                 100                 105

AAG GCG CGC TAC AAT GCT CAG TGC CAG GAG ACC ATC                         385
Lys Ala Arg Tyr Asn Ala Gln Cys Gln Glu Thr Ile
         110                 115                 120

CGC GTC ACC AAG CCC TGC ACC CCC AAG ACC AAA GCA                         421
Arg Val Thr Lys Pro Cys Thr Pro Lys Thr Lys Ala
                 125                 130

AAG GCC AAA GCC AAG AAA GGG AAG GGA AAG GAC TAG                         457
Lys Ala Lys Ala Lys Lys Gly Lys Gly Lys Asp Xaa
         135                 140

ACGCCAAGCC TGGATGCCAA GGAGCCCCTG GTGTCACATG                             497

GGGCCTGGCC ACGCCCTCCC TCTCCCAGGC CCGAGATGTG                             537

ACCCACCAGT GCCTTCTGTC TGCTCGTTAG CTTTAATCAA                             577

TCATGCCCTG CCTTGTCCCT CTCACTCCCC AGCCCCACCC                             617

CTAAGTGCCC AAAGTGGGGA GGGACAAGGG ATTCTGGGAA                             657

GCTTGAGCCT CCCCCAAAGC AATGTGAGTC CCAGAGCCCG                             697

CTTTTGTTCT TCCCCACAAT TCCATTACTA AGAAACACAT                             737

CAAATAAACT GACTTTTTCC CCCCAATAAA AGCTCTTCTT                             777

TTTTAATATA AAAAAAAAA AA                                                 799
```

(3) INFORMATION FOR SEQ ID NO: 2:

(i) SEQUENCE CHARACTERISTICS:
(A) LENGTH: 354 Base Pairs 118 Amino Acids
(B) TYPE: Nucleic Acid and Amino Acid (C) STRANDEDNESS: Single
(D) TOPOLOGY: Linear (ii) MOLECULE TYPE: DNA and Protein (xi) SEQUENCE DESCRIPTION: SEQ ID NO: 2:

| AAA | AAA | AAA | GAG | AAG | GTG | AAG | AAG | GGC | AGC | GAG | TGT | 36 |
|---|---|---|---|---|---|---|---|---|---|---|---|---|
| Lys | Lys | Lys | Glu | Lys | Val | Lys | Lys | Gly | Ser | Glu | Cys | |
| 1 | | | | 5 | | | | | 10 | | | |

| TCG | GAG | TGG | ACC | TGG | GGG | CCC | TGC | ACC | CCC | AGC | AGC | 72 |
|---|---|---|---|---|---|---|---|---|---|---|---|---|
| Ser | Glu | Trp | Pro | Trp | Gly | Pro | Cys | Thr | Pro | Ser | Ser | |
| | | 15 | | | | | 20 | | | | | |

| AAG | GAC | TGC | GGC | ATG | GGC | TTC | CGC | GAG | GGT | ACC | TGT | 108 |
|---|---|---|---|---|---|---|---|---|---|---|---|---|
| Lys | Asp | Cys | Gly | Met | Gly | Phe | Arg | Glu | Gly | Thr | Cys | |
| 25 | | | | 30 | | | | | | 35 | | |

| GGG | GCC | CAG | ACC | CAG | CGC | GTC | CAT | TGC | AAG | GTG | CCC | 144 |
|---|---|---|---|---|---|---|---|---|---|---|---|---|
| Gly | Arg | Gln | Thr | Gln | Arg | Val | His | Cys | Lys | Val | Pro | |
| | | | 40 | | | | | 45 | | | | |

| TGC | AAC | TGG | AAG | AAG | GAA | TTT | GGA | GCC | GAC | TGC | AAA | 180 |
|---|---|---|---|---|---|---|---|---|---|---|---|---|
| Cys | Asn | Trp | Lys | Lys | Glu | Phe | Gly | Ala | Asp | Cys | Lys | |
| | 50 | | | | | 55 | | | | | 60 | |

| TAC | AAG | TTT | GAG | AGC | TGG | GGG | GCG | TGT | GAT | GGG | AGC | 216 |
|---|---|---|---|---|---|---|---|---|---|---|---|---|
| Tyr | Lys | Phe | Glu | Ser | Trp | Gly | Ala | Cys | Asp | Gly | Ser | |
| | | | | 65 | | | | | 70 | | | |

| ACT | GGC | ACC | AAA | GCC | CGC | CAA | GGG | ACC | CTG | AAG | AAG | 252 |
|---|---|---|---|---|---|---|---|---|---|---|---|---|
| Thr | Gly | Thr | Lys | Ala | Arg | Gln | Gly | Thr | Leu | Lys | Lys | |
| | | 75 | | | | | 80 | | | | | |

| GCG | CGG | TAC | ACT | GCC | CAG | TGC | CAG | GAG | ACC | ATC | CGC | 288 |
|---|---|---|---|---|---|---|---|---|---|---|---|---|
| Ala | Arg | Tyr | Thr | Ala | Gln | Cys | Gln | Glu | Thr | Ile | Arg | |
| 85 | | | | | 90 | | | | | 95 | | |

| GTG | ACT | AAG | CCC | TGC | ACC | TCC | AAG | ACC | AAG | TCA | AAG | 324 |
|---|---|---|---|---|---|---|---|---|---|---|---|---|
| Val | Thr | Lys | Pro | Cys | Thr | Ser | Lys | Thr | Lys | Ser | Lys | |
| | | | 100 | | | | | 105 | | | | |

| ACC | AAA | GCC | AAG | AAA | GGA | AAA | GGA | AAG | GAC | | | 354 |
|---|---|---|---|---|---|---|---|---|---|---|---|---|
| Thr | Lys | Ala | Lys | Lys | Gly | Lys | Gly | Lys | Asp | | | |
| | 110 | | | | 115 | | | 118 | | | | |

(4) INFORMATION FOR SEQ ID NO: 3:

(i) SEQUENCE CHARACTERISTICS:
(A) LENGTH: 411 Base Pairs 136 Amino Acids
(B) TYPE: Nucleic Acid and Amino Acid
(C) STRANDEDNESS: Single
(D) TOPOLOGY: Linear (ii) MOLECULE TYPE: DNA and Protein (x) PUBLICATION INFORMATION:
(H) DOCUMENT NUMBER: EP 325 076
(I) FILING DATE: January 24, 1989
(J) PUBLICATION DATE: August 2, 1989
(K) RELEVANT RESIDUES IN SEQ ID NO: 1-19

(xi) SEQUENCE DESCRIPTION: SEQ ID NO: 3:

| GGG | AAG | AAA | GAG | AAA | CCA | GAA | AAA | AAA | GTG | AAG | AAG | 36 |
|---|---|---|---|---|---|---|---|---|---|---|---|---|
| Gly | Lys | Lys | Glu | Lys | Pro | Glu | Lys | Lys | Val | Lys | Lys | |
| 1 | | | | 5 | | | | | 10 | | | |

| TCT | GAC | TGT | GGA | GAA | TGG | CAG | TGG | AGT | GTG | TGT | GTG | 72 |
|---|---|---|---|---|---|---|---|---|---|---|---|---|
| Ser | Asp | Cys | Gly | Glu | Trp | Gln | Trp | Ser | Val | Cys | Val | |
| | | 15 | | | | | 20 | | | | | |

| CCC | ACC | AGT | GGA | GAC | TGT | GGG | CTG | GGC | ACA | CGG | GAG | 108 |
|---|---|---|---|---|---|---|---|---|---|---|---|---|
| Pro | Thr | Ser | Gly | Asp | Cys | Gly | Leu | Gly | Thr | Arg | Glu | |
| 25 | | | | 30 | | | | | | 35 | | |

| GGC | ACT | CGG | ACT | GGA | GCT | GAG | TGC | AAG | CAA | ACC | ATG | 144 |
|---|---|---|---|---|---|---|---|---|---|---|---|---|
| Gly | Thr | Arg | Thr | Gly | Ala | Glu | Cys | Lys | Gln | Thr | Met | |
| | | | 40 | | | | | 45 | | | | |

| | | | | | | | | | | | |
|---|---|---|---|---|---|---|---|---|---|---|---|
| AAG | ACC | CAG | AGA | TGT | AAG | ATC | CCC | TGC | AAC | TGG | AAG | 180
| Lys | Thr | Gln | Arg | Cys | Lys | Ile | Pro | Cys | Asn | Trp | Lys |
| | 50 | | | | 55 | | | | | | 60 |
| AAG | CAA | TTT | GGC | GCG | GAG | TGC | AAA | TAC | CAG | TTC | CAG | 216
| Lys | Gln | Phe | Gly | Ala | Glu | Cys | Lys | Tyr | Trp | Phe | Trp |
| | | | | 65 | | | | | 70 | | |
| GCC | TGG | GGA | GAA | TGT | GAC | CTG | AAC | ACA | GCC | CTG | AAG | 252
| Ala | Trp | Gly | Glu | Cys | Asp | Leu | Asn | Thr | Ala | Leu | Lys |
| | | 75 | | | | | 80 | | | | |
| ACC | AGA | ACT | GGA | AGT | CTG | AAG | CGA | GCC | CTG | CAC | AAT | 288
| Thr | Arg | Thr | Gly | Ser | Leu | Lys | Arg | Ala | Leu | His | Asn |
| 85 | | | | | 90 | | | | | 95 | |
| GCC | GAA | TGC | CAG | AAG | ACT | GTC | ACC | ATC | TCC | AAG | CCC | 324
| Ala | Glu | Cys | Gln | Lys | Thr | Val | Thr | Ile | Ser | Lys | Pro |
| | | | 100 | | | | | 105 | | | |
| TGT | GGC | AAA | CTG | ACC | AAG | CCC | AAA | CCT | CAA | GCA | GAA | 360
| Cys | Gly | Lys | Leu | Thr | Lys | Pro | Lys | Pro | Gln | Ala | Glu |
| | 110 | | | | | 115 | | | | | 120 |
| TCT | AAG | AAG | AAG | AAA | AAG | GAA | GGC | AAG | AAA | CAG | GAG | 396
| Ser | Lys | Lys | Lys | Lys | Lys | Glu | Gly | Lys | Lys | Gln | Glu |
| | | | | 125 | | | | | 130 | | |
| AAG | ATG | CTG | GAT | TAA | | | | | | | | 411
| Lys | Met | Leu | Asp | Xaa | | | | | | | |
| | | 135 | 136 | | | | | | | | |

HUMAN MK GENE AND METHOD OF EXPRESSION

This application is a continuation-in-part of U.S. Ser. No. 07/568,573, filed Aug. 20, 1990, now abandoned.

This invention relates to a novel DNA sequence for a protein having substantial homology to human heparin binding neurotrophic factor (HBNF). The sequences in question also show a high degree of homology with a previously described murine protein designated as MK1. The homology of MK with these known proteins suggests a similar utility in induction of nerve cell growth and differentiation, as well as nerve cell maintenance and repair. Moreover, the occurrence of the MK gene in teratocarcinoma cells and embryonic development indicates broader utility as a differentiation inducing factor, as well as a tissue maintenance or repair factor.

The protein of the present invention is normally produced in the human brain, but apparently at a different time, developmentally, than HBNF. The human MK protein shows about an 85% homology with the published mouse MK sequence. No recognition of the existence of such a protein in humans has previously been made, although it now appears that MK is a member of a highly conserved gene family which is present in a number of different species.

The gene encoding the human MK protein has been isolated from a cDNA library obtained from human newborn brain stem RNA. The gene has been sequenced and cloned; it is a 366-nucleotide sequence predicting a protein having 121 amino acids.

BACKGROUND OF THE INVENTION

Kadomatsu al. (Biochem. Biophys. Res. Comm. 151:1312-1318, 1988) isolated and sequenced cDNA from mouse cells, which they referred to as MK1. The corresponding mRNA was said to be abundant in the early stages of mouse embryonic development, but not in later stages. The MK1 protein was suggested as being associated with control of cell differentiation, specifically as a DNA binding protein regulating gene expression. No relationship to any other known protein sequences was found. A subsequent paper (Tomomura et al., J. Biol. Chem. 265:10765-10770, 1990) reported the expression of the MK gene in early stages of embryonal carcinoma cell differentiation, and also noted the occurrence of three distinct classes of cDNA clones, referred to as MK1, MK2 and MK3. Kadomatsu et al. (J. Cell. Biol. 110:607-616, 1990) suggested MK may play a fundamental role in the differentiation of a variety of cells, and that it may be involved in the generation of epithelial tissues and in the remodeling of mesoderm.

The mouse MK1 sequence has now been found to have a high degree of homology in the group of proteins known as heparin-binding neurotrophic factors (HBNFs); the nucleotide sequence encoding the latter proteins has been disclosed in applicants' copending and cofiled U.S. Ser. No. 07/568,574. The HBNF proteins were originally disclosed as HBBMS, in EP 325076. It has now been unexpectedly discovered that a gene corresponding to the mouse MK sequence is also found in human brain. The present invention provides the entire sequence of the gene encoding the human protein, as well as the predicted amino acid sequence of the mature protein, cloning and expression vectors, and host cells capable of expressing the gene and producing pure MK protein. In view of the strong homology between the MK proteins and HBNF, it is likely that these constitute a family of genes and proteins having developmental significance.

BRIEF DESCRIPTION OF THE DRAWINGS

FIG. 1 (See also Sequence Listing 1). Nucleotide and amino acid sequence of the human MK gene. Boldfaced amino acids represent the predicted protein presequence, the arrow represents the predicted N-terminus of the mature protein, and the two peptide sequences corresponding to primers 1 and 2 used to amplify the mouse genomic DNA probe are underlined. The two polyadenylation sequences near the 3' end of the gene are underlined.

FIG. 2 and continuation of FIG. 2 shows a comparison of the mature protein region of human HBNF (See also Sequence Listing 3) and MK nucleotide and deduced amino acid sequence. Identical amino acids are indicated in bold letters. Identities in the two nucleotide sequences are indicated by stars (*).

FIG. 3 shows a nucleotide sequence and deduced amino acid sequence of human and mouse MK (See also Sequence Listing 2). Differences in the two nucleotide sequences are indicated by stars (*). Differences in the amino acids are indicated in bold letters. Amino acids used in the mouse genomic PCR primer design are underlined.

FIG. 6 shows (a) Expression of HBNF gene during rat embryogenesis From each tissue 20 ug total RNA was applied per lane and hybridized with a $^{32}$P-labeled human HBNF cDNA probe. Tissues used in the RNA isolation were total embryo proper for E8 and E10, heads for E12 and E14, total brain for E16, E18, E20, P2 and Adult; (b) Expression of MK gene during rat embryogenesis. Same northern blot as in (a) hybridized with a $^{32}$P-labeled human MK cDNA probe.

DETAILED DESCRIPTION OF THE INVENTION

The DNA sequence encoding human MK is cloned by isolating a combination of polymerase chain reaction (PCR) and screening of a cDNA library derived from newborn human brain stem. The human HBNF sequence is used as the starting point for designing oligonucleotides for a PCR amplification reaction; this sequence is shown in FIG. 2. Specific oligonucleotides are designed to the regions most conserved between HBNF and the published mouse MK1 DNA sequence. These oligonucleotides are used as primers in a polymerase chain reaction (PCR) on mouse genomic DNA. The expected 150 base pair product is cloned in an appropriate vector and the sequence determined. This clone is used as a probe for screening a human brain cDNA library to identify the human MK equivalent gene. A single clone is isolated, subcloned and sequenced. The sequence of one of these clones is shown in FIG. 1, and accounts for 790 nucleotides of the estimated 1100 nucleotides of mature human MK mRNA. The nucleotide sequence is subsequently confirmed in additional shorter-length MK clones, which are found to contain different overlapping fragments of the original clone. The sequence of the MK cDNA includes two polyadenylation signals and a poly A tail (FIG. 1). The original isolated clone has an open reading frame with a coding region beginning at nucleotide 22 and defining a 143 residue protein. The N-terminal sequence is highly hydrophobic and has the characteristics of a signal peptide (Von Heijne, J. Mol. Biol. 184:99–105, 1985). On the basis of the criteria for signal peptide structures set forth by Von Heijne (id; Nucl. Acid Res. 14:4683–4690, 1986) and comparisons with mouse MK and human HBNF sequences, it is assumed that signal peptide cleavage occurs between amino acid residues 22 (Ala) and 23 (Lys), thus giving rise to a mature MK polypeptide of 121 residues in length.

As shown in FIG. 3, a comparison of the human MK deduced amino acid sequence with the mouse MK protein sequence indicates a difference of only about 15%. Most of these changes are conservative. The homology between MK and HBNF, shown in FIG. 2, indicates a homology of 50%, increasing to 63% when conserved amino acid changes are included. Ten Cysteines which are present in both proteins are perfectly aligned, suggesting similar structures.

Figure 4:
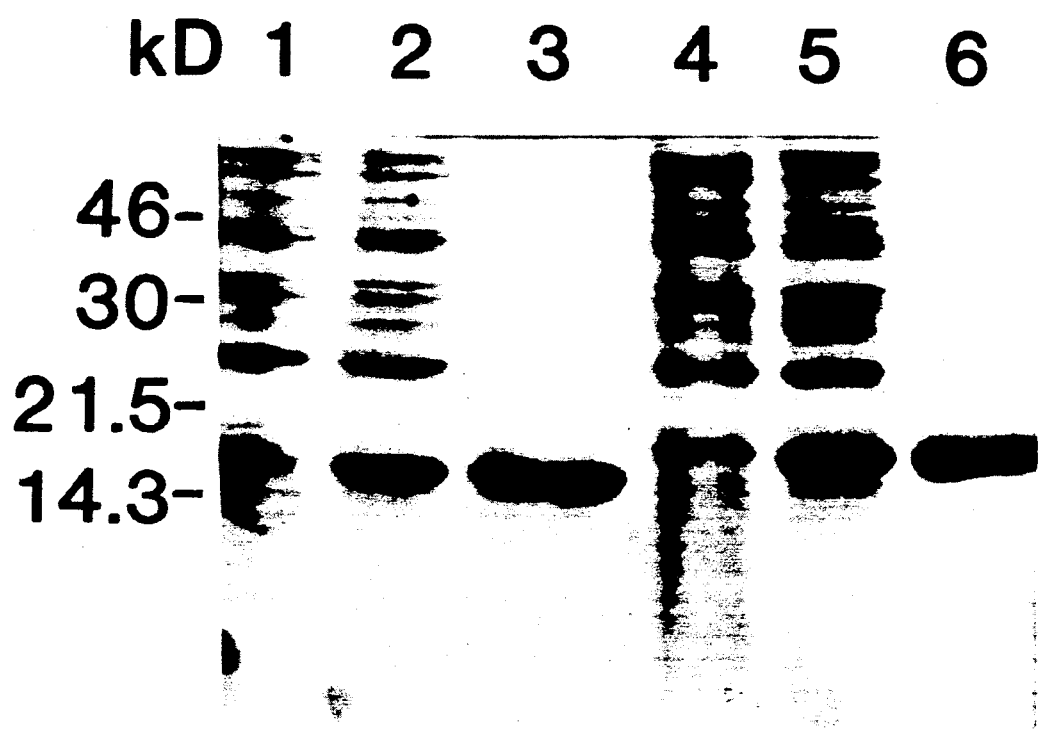
FIG. 4. Bacterial Expression of human recombinant HBNF and MK proteins. Cell lysates are from bacterial cultures containing the expression plasmids pETHH8 or pETMH2. Lanes 1 and 2, lysates from uninduced and IPTG-induced cultures containing pETMH2. Lane 3, purified recombinant MK protein Lanes 4 and 5, uninduced and induced cultures containing pETHH8. Lane 6, purified recombinant HBNF protein. Protein standards are from BRL.

To provide a source of the mature MK protein free of contaminating eukaryotic proteins, cDNA clones isolated above are used as templates for PCR amplification with primers designed to place a methionine codon immediately 5' of the N-terminal lysine residue of the mature proteins. The amplified product is cloned into a modified form of the expression vector pET-3a (Studier, et al., 1990), and the resulting plasmid pETMH2 is transformed into E. coli strain BL21 LysS. Protein extracts of IPTG-induced pETMH2-containing bacteria express a major protein band migrating at approximately 16.5 kDa (FIG. 4, Lane 2). Uninduced culture (Lane 1, pETMH2-containing bacteria) contains much less of the protein as judged by SDS-PAGE band intensities. Recombinant MK protein is purified from IPTG-induced bacterial cultures by heparin affinity chromatography (FIG. 4, Lane 3) and its N-terminal sequence and amino acid compositions confirmed.

Figure 7:
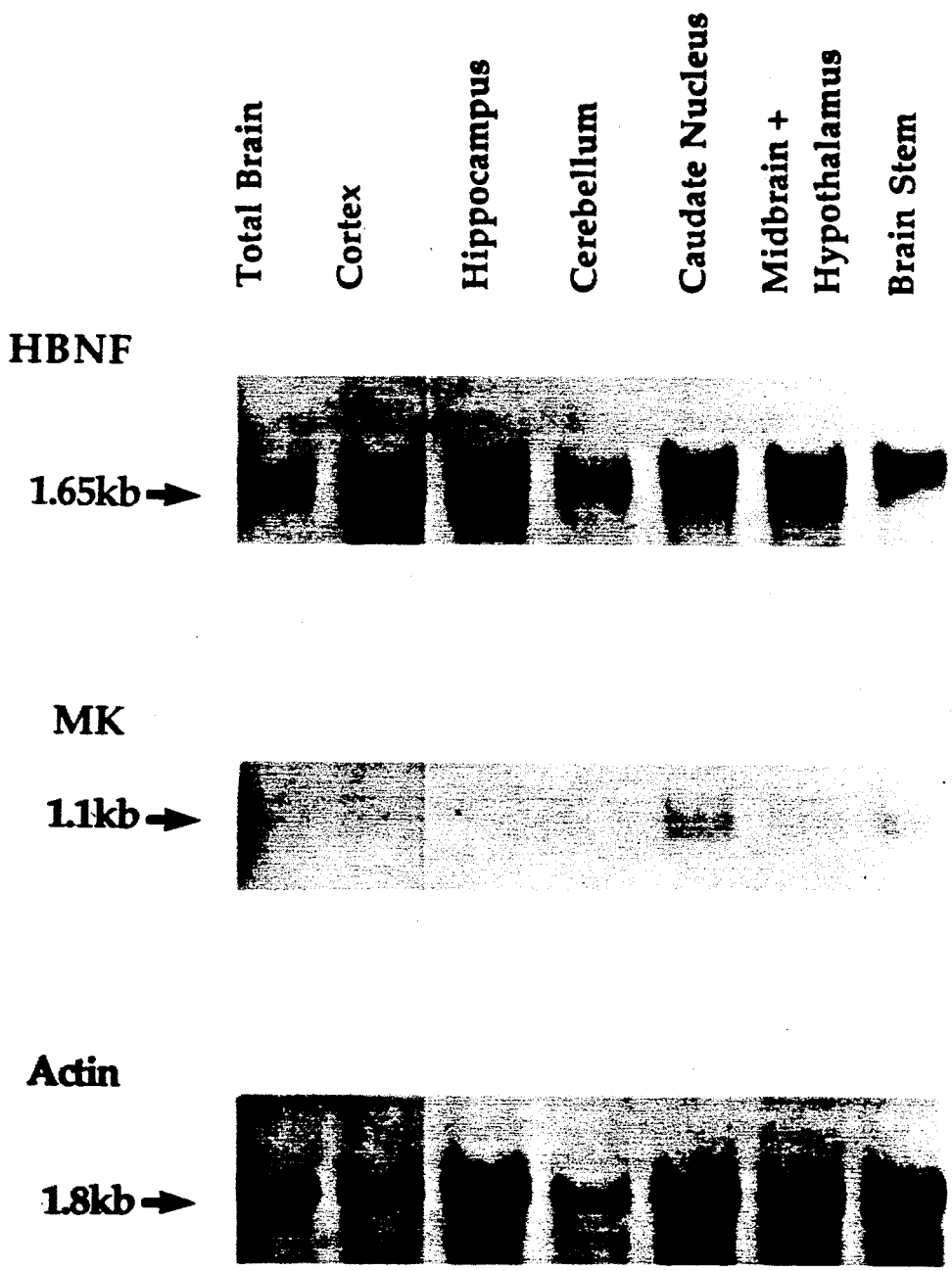
FIG. 7. Gene expression of HBNF and MK in the adult rat brain. RNA extracted from various brain regions of 2-month-old rats was subjected to northern analysis (10 μg/lane of RNA; Lane 1—total brain, 2—cortex, 3—hippocampus, 4—cerebellum, 5—caudate nucleus, 6—midbrain+hypothalamus, 7—brain stem). The resulting blot was hybridized consecutively to probes for HBNF, MK and β-actin.

Homology between the human and published mouse MK DNA and the deduced protein sequences show a lower level of conservation than a similar evolutionary comparison of HBNF (FIG. 3). Using a putative N-terminus from the mature MK protein deduced from homology with HBNF, 86% amino acid identity is observed including a three amino acid deletion in the mouse sequence. Both HBNF and MK are expressed in brain but their temporal and spatial regulation differs. Preliminary in situ hybridization showed distinct patterns of expression for the two messages. Northern hybridization analysis of mouse RNA from the adult tissues examined indicates that only brain expressed a 1650-nucleotide HBNF message (FIG. 6). This is consistent with previous investigations on the expression characteristics of the HBNF protein which show it is present in the brain (EP 326 075, Rauvala, EMBO J. 8:2933–2941, 1989). Recently, HBNF protein was also isolated from bovine uterus (Milner et al. Biochem. Biophys. Res. Comm. 165:1096–1103, 1989). These initial experiments indicated that MK is not expressed in any adult tissue examined (FIG. 6). However, subsequent experiments indicate that MK mRNA is detectable in two regions of the adult brain, the caudate nucleus and the brain stem (FIG. 7). Based on the significantly longer exposure times needed to see these bands in adult RNA as compared to equivalent amounts of embryonic RNA, it appears that MK RNA is expressed at minimal levels in the adult.

The temporal expression of both genes is evaluated by northern blot analysis with total rat RNA from various developmental stages. Hybridization with an HBNF probe indicates a gradual increase of message throughout development, with the highest level occurring in the adult brain (FIG. 6a). Hybridization of the same blot with an MK probe indicates that only 12-, 14- and 16-day embryonic tissues contained the message. The most abundant presence of MK message appears to be in the embryonic day 12 stage (FIG. 6b). These results are in general agreement with the in situ hybridization studies of Kadomatsu (supra). However, contrary to the findings of Kadomatsu, we were unable to detect MK mRNA expression in kidney tissue. Studies of HBNF protein in rat brains suggest that the highest level occurs in postnatal day-7 pups. This level reflects a ten-fold difference when compared to 56-day old animals (Rauvala, supra).

Figure 8A:
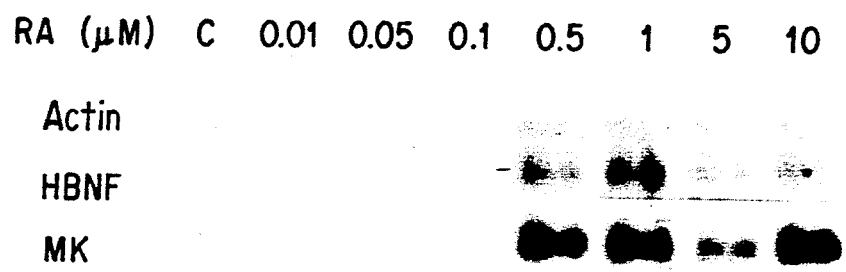
FIG. 8 (parts A and B). Retinoic acid-induced expression of HBNF and MK genes in NT2/D1 cells. NT2/D1 cells were treated with varying concentrations of RA, grown for 9 days, and RNA extracted. (A) For each RA concentration of 10 μg of RNA was used in northern analysis. The resulting blot was consecutively hybridized with HBNF, MK and β-actin probes. (B) Hybridization signals obtained in (A) for HBNF (black) and MK (hatched) were measured by densitometry and normalized to the β-actin signals.
Figure 8B:
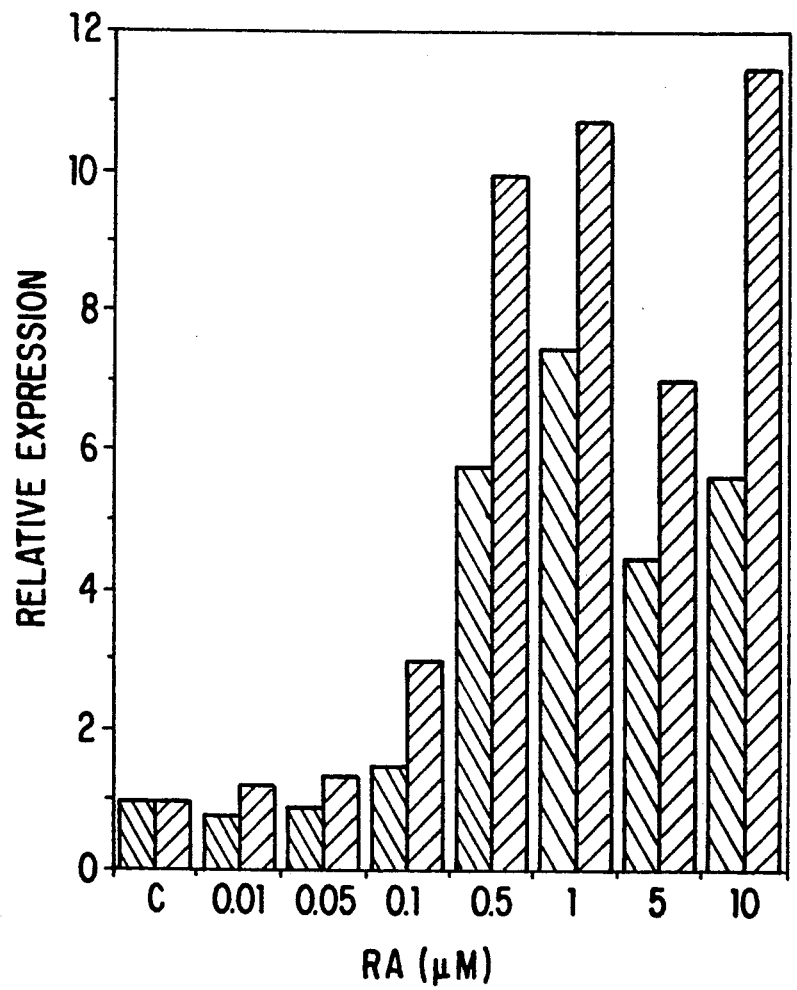

The human embryonal carcinoma (EC) cell line NT2/D1 can be induced to differentiate at concentrations of retinoic acid (RA) varying from 0.01 to 10 μM, with the proportion of differentiating EC cells ranging from 50% at 0.01 μM RA (Simeone, et al., Nature 346:763–766, 1990) to greater than 99% at 1 and 10 μM RA (Andrews, Dev. Biol. 103:285–293, 1984). The expression of MK and HBNF during differentiation of NT2/D1 is studied, at concentrations ranging from 0.01 to 10 μM. After nine days of exposure to RA, total RNA was extracted from cells and probed for gene expression by northern analysis. Expression of both genes followed a similar pattern (FIG. 8). Levels of mRNA expression remained at a steady background level with 0.1–0.5 μM RA, rapidly increased between 0.1 and 0.5 μM RA, and maintained this level at concentrations up to and including 10 μM RA. When RNA hybridization signals were normalized to a control β-actin probe, the maximum increases were calculated to be 6-fold for HBNF and 11-fold for MK (FIG. 8). These results are comparable to those observed for MK during retinoic acid induction of the mouse EC cell line, HM-1 (Kadomatsu et al., supra). In this cell line, MK gene expression was induced 8-10 fold above background.

Recombinant HBNF and MK proteins are assayed for the ability to stimulate neurite outgrowth of 18-day fetal rat brain neurons. Both bacterially-derived proteins showed neurite outgrowth-promoting activity similar to that of native bovine HBNF (FIG. 5). The recombinant MK protein is also assayed for mitogenic activity on adult bovine aortic endothelial cells and NIH 3T3 fibroblasts. MK protein shows no mitogenic activity on these cells. However, conditioned medium from MK-transfected L cells has been reported to be mitogenic from PC12 cells by Tomomura (Biochem. Biophys. Res. Comm. 171: 603, 609, 1990).

The findings of the present invention thus indicate that HBNF and MK are members of a highly conserved gene family. Furthermore, the gene expression data implies that these genes function in the proliferation, maintenance and/or developmental differentiation of tissue and, in particular, nerve tissue.

The following examples illustrate the cloning and expression of the MK gene in a T7 RNA polymerase expression system. However, although this T7 expression system is quite efficient, it is to be understood that this is not the only means by which MK can be produced recombinantly. Production of MK can be achieved by incorporation of the MK gene into any suitable expression vector and subsequent transformation of an appropriate host cell with the vector; alternately the transformation of the host cells can be achieved directly by naked DNA without the use of a vector. Production of MK by either eukaryotic cells or prokaryotic cells is contemplated by the present invention. Examples of suitable eukaryotic cells include mammalian cells, plant cells, yeast cells and insect cells. Similarly, suitable prokaryotic hosts, in addition to *E. coli*, include *Bacillus subtilis*.

Other suitable expression vectors may also be employed and are selected based upon the choice of host cell. For example, numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the MK gene as defined in FIG. 1. Modifications to the sequence, such as deletions, insertions, or substitutions in the sequence which product silent changes in the resulting protein molecule are also contemplated. For example, alterations in the gene sequence which result in the production of a chemically equivalent amino acid at a given site are contemplated; thus, a codon for the amino acid alanine, a hydrophobic amino acid, can readily be substituted by a codon encoding another hydrophobic residue, such as glycine, or may be substituted with a more hydrophobic residue such a valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule frequently do not alter protein activity, as these regions are usually not involved in biological activity. It may also be desirable to eliminate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of biological activity of the encoded products. Therefore, where the phrase "MK DNA sequence" or "MK gene" is used in either the specification or the claims, it will be understood to encompass all such modifications and variations which result in the production of a biologically equivalent MK protein. In particular, the invention contemplates those DNA sequences which are sufficiently duplicative of the sequence of FIG. 1 so as to permit hybridization therewith under standard high stringency southern hybridization conditions, such as those described in Maniatis et al., (Molecular Cloning. A Laboratory Manual Cold Spring Harbor Laboratory, 1982). The MK protein is strongly homologous to the HBNF protein and, like HBNF, stimulates induction of neurite outgrowth. MK is, therefore, proposed as a neurotrophic agent. As such, the MK proteins are useful both in vivo and in vitro, in growth, maintenance and repair of nerve cells of the peripheral and central nervous systems. An example of in vitro application is in maintenance of embryonic brain implants which are now proposed for use in treatment of Parkinson's disease.

In view of the apparent role in differentiation, the MK protein is also proposed as a general tissue differentiation, maintenance and repair factor. In particular, MK may be useful in treatment of tumor cells to induce reversion to a differentiated phenotype.

In vivo administration of MK is significantly simplified by the discovery of the gene sequence, particularly in treatment of central or peripheral nervous system injury. The identification of the gene and its sequence permit construction of transgenic cells such as fibroblasts, monocytes, or macrophages, which may be engineered to permit expression of the MK gene and used as an implant for treatment of neurodegenerative disorders, peripheral nerve repair following surgery, or any conditions in which enhancement of nerve cell growth and/or repair would be desirable.

Moreover, the therapeutic use of MK is not limited to treatment of humans alone. In fact, in view of the conserved nature of this protein among distantly related species, administration of MK in any form may be beneficial for veterinary application as well. Therapeutic compositions comprise MK in an amount effective to induce the desired biological activity in combination with a pharmaceutically acceptable liquid or solid carrier. Alternately, the composition comprises a pharmaceutically acceptable aggregation of compatible transgenic cells capable of expressing MK in vitro, as an implant for peripheral and central nervous system repairs or differentiation treatment.

EXAMPLE

Cloning and Sequencing of the MK Gene

The published mouse MK protein amino acid sequence was used to create specific oligonucleotides to be used as primers in a polymerase chain reaction. Mouse genomic DNA was isolated from C57 Black/6J mice, as described in Maniatis et al. supra.

A sense primer is made to the amino acid sequence: CNWKKEFG (FIG. 1) starting with a HindIII restriction site and comprised of the DNA sequence: 5'GGAATTCGGTCTCCTGGCACTGGGCAGT-3'.

The PCR reaction is carried out on the complementary DNA template with a minute annealing at 50° C., 2 minutes extension at 72° C. and 1 minute denaturation at 94° C. for 30 cycles using Taq polymerase (USB Corp.)

The 150 base pair mouse MK PCR product is cloned into Blue Scribe (+) vector (Stratagene) and used as a probe in screening a newborn brain stem and basal ganglia λ gt 11 cDNA library (Kamholz, PNAS USA 83:4962–54966, 1986). A single putative clone containing the MK sequence is isolated and subcloned into the EcoRI site of Blue Scribe (+) and sequenced by the dideoxynucleotide chain termination method (Sanger et al. PNAS USA 74:5463–5467, 1988) The sequence of the MK gene, as well as the predicted amino acid sequence is presented in FIG. 1. Comparison with the mouse MK sequence shows a 41 nucleotide difference, including the three codon deletion in the mouse sequence.

EXPRESSION OF RECOMBINANT HUMAN MK

The isolated clone noted above, referred to as pMKHC2 is used as a template for PCR amplification with primers designed to place a methionine codon and an Nde I restriction site immediately 5' to the N-terminal lysine. The purified PCR product is cloned into a derivative of the expression vector pET-3a, which is modified by the deletion of the 1400 bp Sal1/PvuII fragment and insertion of an fl origion of replication into the EcoRI site. After sequencing the insert to confirm the fidelity of the PCR amplification, the plasmid (named pETMH2; also previously referred to as pETMKHC2) is transformed into strain BL21 lysS and induced for protein production with IPTG as described (Studier et al., supra). Pellets from one ml culture are resuspended in 100 µl of SDS buffer (Laemmli, Nature 227:680–685, 1970) and 2.5 µl run on a 15 acrylamide SDS-PAGE gel. The gel is stained with coomassie blue. Recombinant MK is purified from bacterial extract on heparin sepharose CL-6B (Pharmacia) resin in 10 mM Tris, pH 7.0 and eluted at 1–1.13M NaCl. Further purification is achieved on Mono S (Pharmacia) columns in 50 mM sodium phosphate, pH 6.8, with increasing salt concentration from 0 to 1M NaCl. Purified protein is eluted at 0.6M NaCl.

NEURITE OUTGROWTH ASSAYS

Figure 5A:
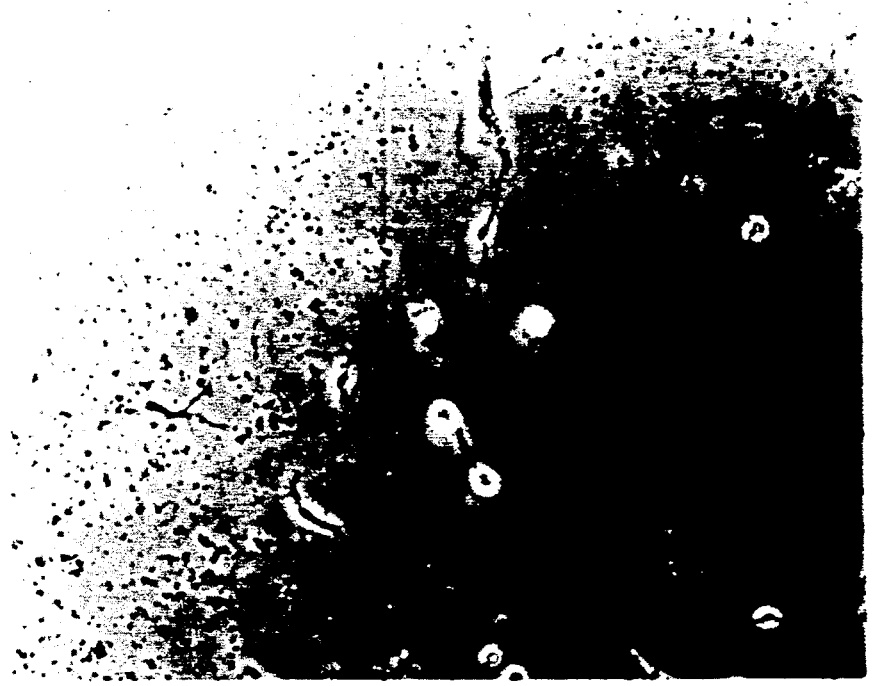
FIG. 5 (parts A-D). Neurite outgrowth assays of purified recombinant HBNF and MK proteins. Purified proteins are assayed on 18-day fetal rat neurons at concentrations indicated. (A) Neuronal cells with no added protein (b) Bovine brain-derived HBNF protein (160 ng/ml). (C) Purified recombinant human HBNF protein (150 ng/ml). (d) Purified recombinant human MK protein (150 ng/ml)
Figure 5B:
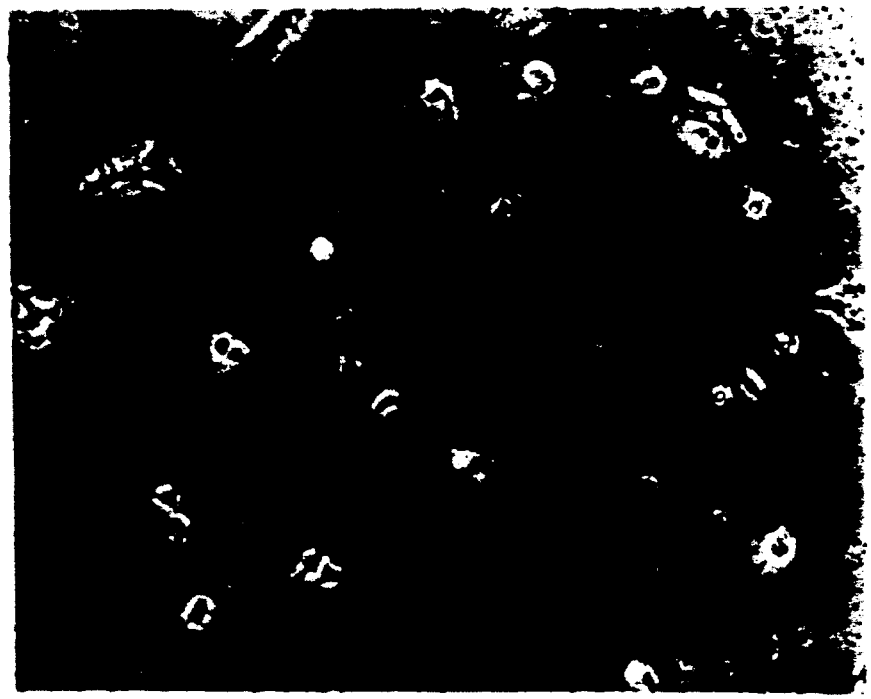
Figure 5C:
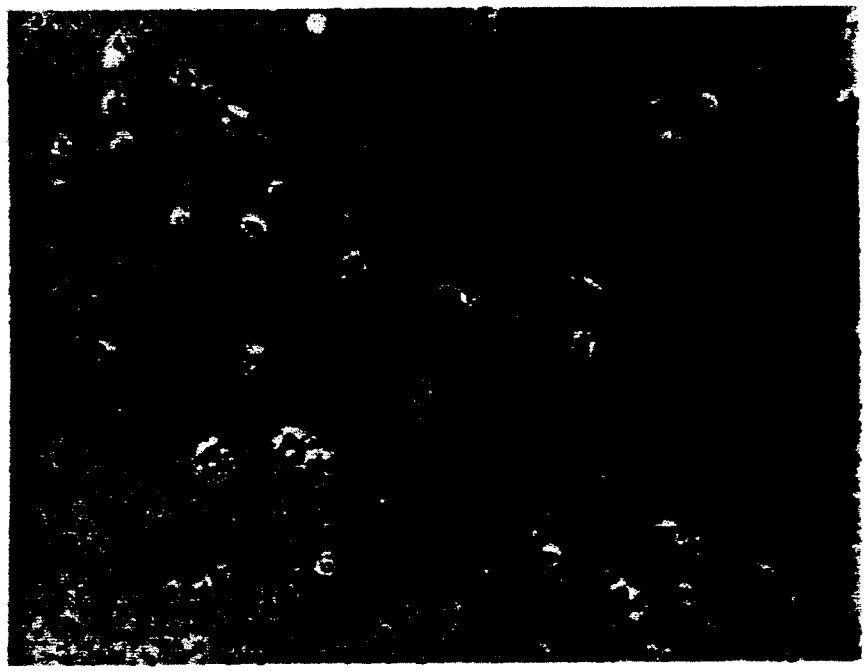
Figure 5D:
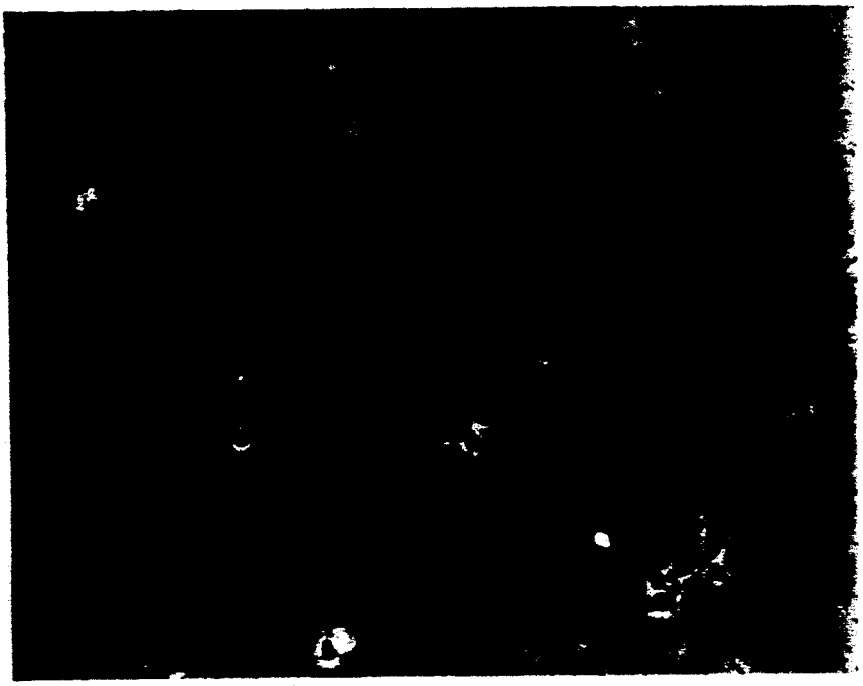

Brains from 18-day fetal rats are removed under sterile conditions and dispersed to single cells in DMEM containing 10% FCS using a sterile 5 ml syringe. The cell suspension as adjusted to $5 \times 10^5$ cells/ml and plated onto tissue culture dishes that are precoated with 50 µg/ml poly-L-lysine for 30 minutes at room temperature (Rauvala and Pihlaskari, J. Biol. Chem. 262:16625–16635, 1987). Cultures are incubated for 24 hours at 37° C. in 10% $CO_2$, after which the media is changed to DMEM containing 1 mg/ml BSA, and HBNF or MK proteins are added at indicated concentrations. After a further one-day incubation, neurite outgrowth activity is determined by visual examination of cells for extended outgrowth/processes as compared to controls. As shown in FIG. 5D, purified recombinant MK is capable of stimulating neurite outgrowth to substantially the same extent as recombinant HBNF and bovine brain derived HBNF.

GROWTH AND RETINOIC ACID INDUCTION OF THE HUMAN NT2/D1 CELLS

The human embryonal carcinoma cell line NT2/D1 is grown as described previously (Andrews, Dev. Biol. 103:285–293, 1984). For retinoic acid induction, cells are grown and resuspended in DMEM medium containing 10% bovine calf serum and resuspended in DMEM medium containing 10% bovine calf serum (Hyclone Laboratories, Inc.) at a density of $5 \times 10^5$ cells per 100 mm dish. Varying concentrations of all-trans retinoic acid in dimethyl sulfoxide (10 µl) is added, and cells are incubated for 9 days. Fresh medium and RA are added at days 4 and 8. Plates are washed once with phosphate buffered saline, and RNA extracted as described above. FIG. 8 shows a graphic representation of the levels of both HBNF and MK produced in response to varying levels of retinoic acid concentration. Since NT2/D1 cells induced with RA have been suggested as providing a model system for studies of neuronal differentiation (Lee and Andrews, J. Neurosci. 6:514–521, 1986), the increase in induction of HBNF and MK genes in this system indicates a possible role in neuronal cell development.

DEPOSIT OF BIOLOGICAL MATERIALS

E. coli strain M 1061 harboring pMKHC2 and E. coli strain BL2T LysS harboring pETMH2 have been deposited in the culture collections of American Cyanamid Company, Lederle Laboratories, Pearl River, N.Y., and with the American Type Culture Collection, 12301 Parklawn Drive, Rockville, Md., under accession number ATCC 68384, on Aug. 13, 1990 and accession number 68401, on Sep. 17, 1990, respectively.

We claim:

1. A purified and isolated nucleic acid sequence encoding a human MK protein, wherein the sequence is hybridizable under standard high stringency conditions with a nucleic acid sequence encoding the amino acid sequence depicted in FIG. 1.

2. The sequence of claim 1 which has the MK sequence depicted in FIG. 1, or a portion thereof, which encodes a biologically active MK protein.

3. A method for production of substantially pure MK protein which comprises transforming a host cell with the sequence of claim 1 and culturing the host cell under conditions which permit expression of the gene by the host cell.

4. The method of claim 3 in which the bacterial cell is E. coli.

5. The method of claim 5 in which the vector is pETMH2.

6. An expression vector comprising the sequence of claim 2.

7. The vector of claim 6 which is a virus, a plasmid, a yeast vector, or a bacteriophage.

8. The vector of claim 7 which is a plasmid.

9. The vector of claim 8 which is pETMH2.

10. A host cell comprising the sequence of claim 1.

11. The cell of claim 10 which is E. coli.

12. The cell of claim 11 which comprises a plasmid vector.

13. The cell of claim 12 which is deposited with the American Type Culture Collection as ATCC 68384.

14. The cell of claim 12 which is deposited with the American Type Culture Collection as ATCC 68401.

* * * * *

UNITED STATES PATENT AND TRADEMARK OFFICE
CERTIFICATE OF CORRECTION

PATENT NO. : 5,210,026
DATED : May 11, 1993
INVENTOR(S) : Imre Kovesdi and Peter Bohlen It is certified that error appears in the above-indentified patent and that said Letters Patent is hereby corrected as shown below:

Column 14, Claim 5, line 29, cancel "claim 5" insert --claim 4--.

Signed and Sealed this

Twenty-fifth Day of January, 1994

*Attest:*

BRUCE LEHMAN

*Attesting Officer*     *Commissioner of Patents and Trademarks*